United States Patent [19]
Baer

[11] Patent Number: 5,493,741
[45] Date of Patent: Feb. 27, 1996

[54] PATIENT SUPPORT OPERABLE IN COMBINATION WITH A PATIENT GURNEY FOR MEDICAL EXAMINATIONS

[75] Inventor: Ulrich Baer, Neunkirchen, Germany

[73] Assignee: Siemens Aktiengesellschaft, Munich, Germany

[21] Appl. No.: 285,423

[22] Filed: Aug. 4, 1994

[30] Foreign Application Priority Data

Sep. 9, 1993 [DE] Germany .......................... 43 30 606.3

[51] Int. Cl.$^6$ ............................... A61G 7/10; A61G 7/00
[52] U.S. Cl. ...................... 5/86.1; 5/81.1; 5/601
[58] Field of Search ....................... 5/81.1, 601, 600, 5/86.1; 378/209

[56] References Cited

U.S. PATENT DOCUMENTS

| | | | |
|---|---|---|---|
| 2,681,839 | 6/1954 | Limbach | 5/601 |
| 3,099,020 | 7/1963 | Garfield et al. | 5/620 |
| 3,504,386 | 4/1970 | Rossi | 5/81.1 |
| 3,902,204 | 9/1975 | Lee | 5/81.1 |
| 4,105,923 | 8/1978 | Hynes, Jr. | 5/601 |
| 4,277,218 | 7/1981 | Schweider | 5/617 |

FOREIGN PATENT DOCUMENTS

| | | | |
|---|---|---|---|
| 3034932 | 4/1983 | Germany | 5/81.1 |
| 4224036 | 5/1993 | Germany | 5/81.1 |

OTHER PUBLICATIONS

Siemens Sales Brochure "Koordinat Kombi" Date Unknown.

*Primary Examiner*—Alexander Grosz
*Attorney, Agent, or Firm*—Hill, Steadman & Simpson

[57] ABSTRACT

A patient support of the type which is used for conducting medical examinations has a base with a patient support plate thereon. A gurney, for bringing a patient to the patient support to conduct an examination, has a carriage with its own patient support plate. The gurney is positioned adjacent to the patient support and the patient is transferred from the gurney to the patient support while remaining on the gurney support plate, the gurney support plate being held on the patient support by bearings. The gurney support plate is attached to the gurney carriage by a longitudinal guide, so that the gurney support plate is adjustable along its longitudinal axis. The gurney support plate can then be longitudinally co-displaced with the support plate of the apparatus patient support, so that it need not be detached from the carriage.

5 Claims, 3 Drawing Sheets

5,493,741

PATIENT SUPPORT OPERABLE IN COMBINATION WITH A PATIENT GURNEY FOR MEDICAL EXAMINATIONS

BACKGROUND OF THE INVENTION

1. Field of the Invention

The present invention is directed to a patient support of the type employed for medical examinations, which can be used in combination with a patient gurney.

2. Description of the Prior Art

The combination of a patient support operable in combination with a patient gurney is disclosed in German PS 42 24 036, the basic elements of which are shown in FIG. 1 herein. The gurney in this known combination has a carriage 1 with a first support plate 2, on which an examination subject lies. The examination subject 3 can thus be moved by means of the carriage 1 to bring the examination subject 3 to an examination room wherein a medical examination, such a computer tomography examination, is to be undertaken. The medical examination apparatus has a patient support which includes a base 4 having a second support plate 5, onto which the examination subject 3 can be transferred. The base 4 is stationary, but the support plate 5 thereof is at least longitudinally displaceable so that the second support plate 5, together with the examination subject 3 thereon, can be introduced into the opening 6 of a medical apparatus such as a computer tomography apparatus. Healthy examination subjects can place themselves on the second support plate 5 prior to an examination, without assistance. A seriously injured examination subject or a bedridden examination subject, however, must be transferred in some manner from the first support plate 2 on the carriage 1 to the second support plate 5 on the base 4. To assist in this transfer, the carriage 1 in the known combination shown in FIG. 1 has a U-shaped frame, and the carriage 1 is positioned relative to the base 4 so that the U-shaped frame embraces the base 4 of the apparatus patient support. Guide means can be provided for this purpose on the U-shaped frame, and possibly on the base 4, so that the carriage 1 is arranged in a position relative to the base 4 so that the first support plate 2 is located above the second support plate 5. The patient transfer can ensue either by lowering the first support plate 2, by means of a lifting mechanism provided on the carriage 1, or the second support plate 5 can be raised by a lifting mechanism arranged in the base 4. When this occurs, the first support plate 2 becomes detached from the carriage 1, so that the first support plate 2 lies on the second support plate 5. Bearings, such as pins engaging into recesses, can be provided for positioning the support plates 2 and 5 relative to each other. After support plate 2 has been accepted onto the support plate 5, the carriage I can be removed, and the examination subject 3 can be introduced for conducting an examination into the opening 6 of he medical apparatus 7 by means of the base 4 displacing the support plate 5, and thus also the support plate 2, along their longitudinal axes.

Bases, such as the base 4, for patient support arrangements in medical systems are known which have a telescoping upper portion, carrying a support plate such as the support plate 5, which is also movable in the longitudinal direction of the support plate 5 relative to the base 4. Such longitudinal displacement of the upper part, however, can ensue in the known arrangement of FIG. 1 only when the carriage 1 of the gurney has been detached from the base 4, after transfer of the first support plate 2 onto the second support plate 5.

SUMMARY OF THE INVENTION

It is an object of the present invention to provide the combination of a medical apparatus patient support operable with a patient gurney for conducting a medical examination wherein longitudinal displacement o the support plate of the apparatus patient support can take place without detachment of the gurney patient support from its carriage.

The above object is achieved in accordance with the principles of the present invention in an apparatus patient support operable in combination with a patient gurney wherein the support plate of the gurney is attached to its carriage by means of longitudinal guides, which permit the carriage to remain in place embracing the base of the apparatus patient support while both the apparatus support plate and the gurney support plate are simultaneously longitudinally displaced.

An advantage of the invention is that the first support plate is mounted the carriage in a manner so as to be adjustable along its longitudinal axis by means of the longitudinal guides, so that adjustment of the first and second support plates into the opening of the medical apparatus is possible without the carriage having to be uncoupled from the base. If the base is of the type having a telescoping, adjustable upper part, it is advantageous to attach the gurney support plate to a frame of the carriage via the longitudinal guides. The longitudinal guides can then be received in cross beams at the ends of the carriage. The frame can thus support itself at the upper part of the base, and is adjustable together with the upper part in the longitudinal direction of the carriage, without an uncoupling of the carriage from the base being required.

The longitudinal guides can extend over the entire longitudinal length of the carriage, or may occupy only a portion of the length of the carriage.

In a less complicated embodiment, the longitudinal guides can be formed by rails arranged at the carriage which are vertically offset relative to each other.

DESCRIPTION OF THE PREFERRED EMBODIMENTS

Figure 1:
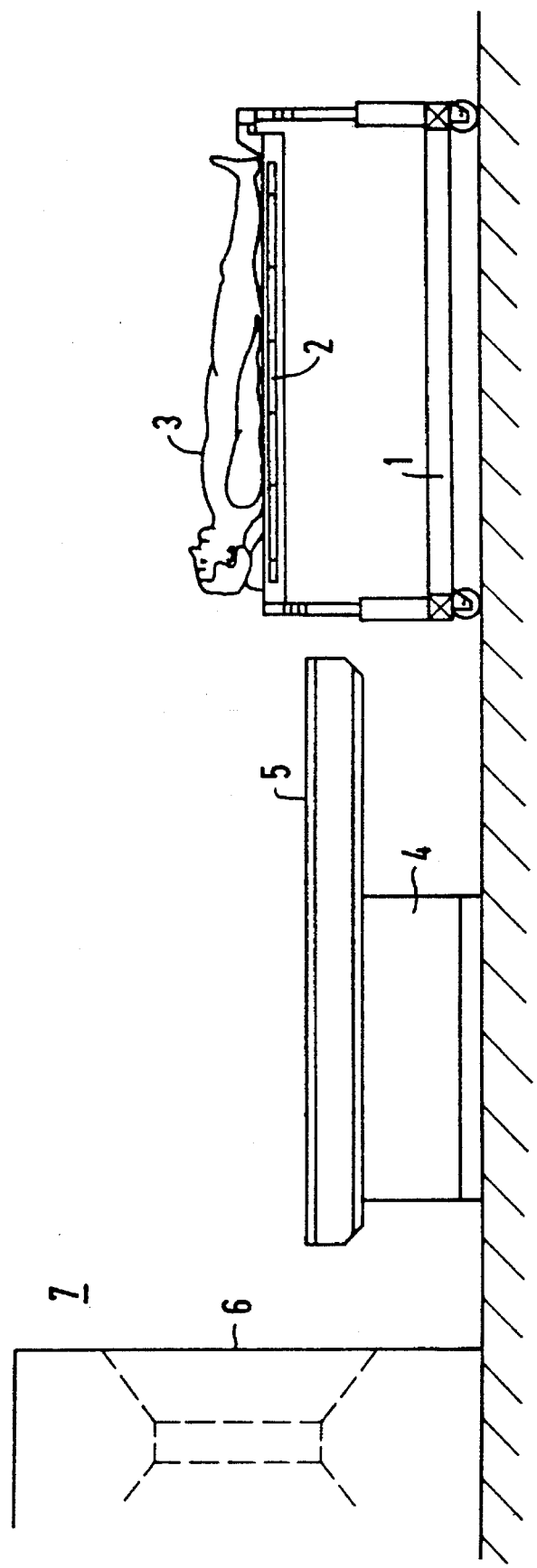
FIG. 1, as noted above, shows a known patient support apparatus according to German PS 42 24 036.
Figure 2:
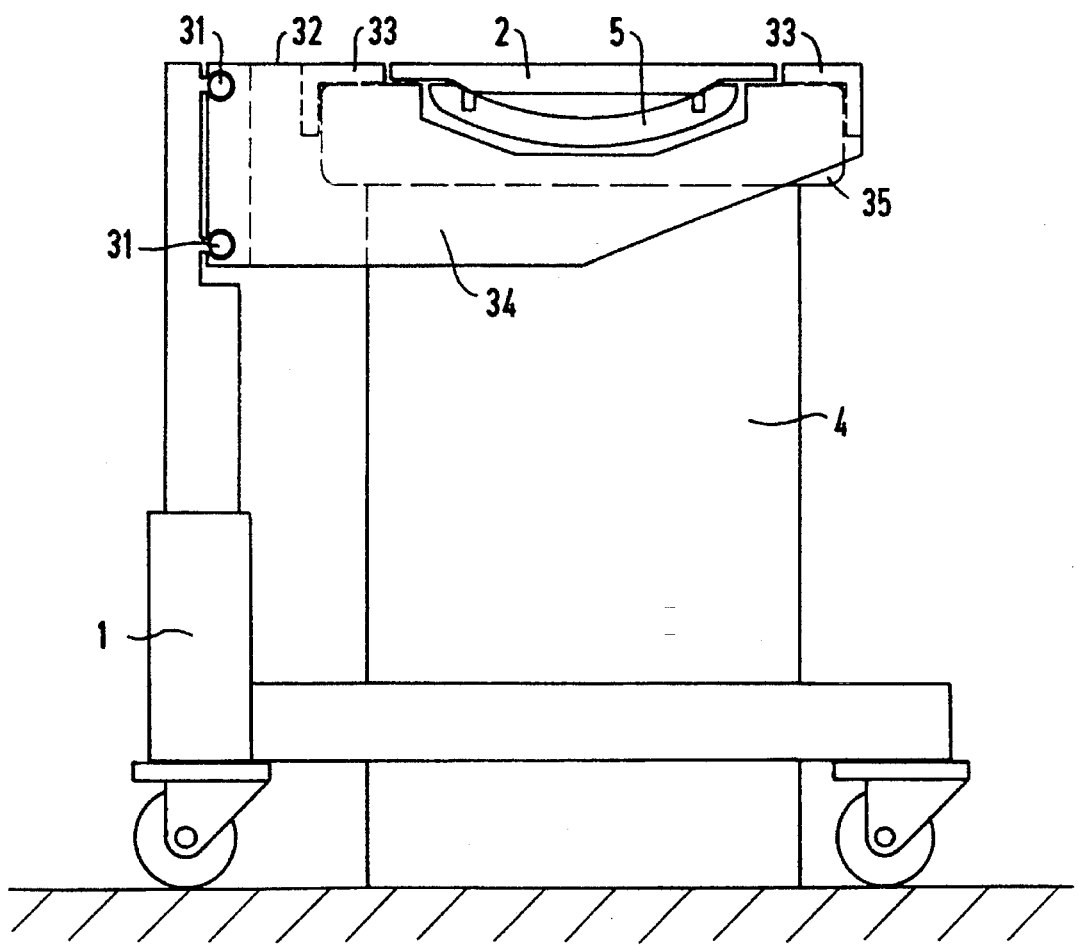
FIG. 2 is an end elevational view of a patient support operable in combination with a patient gurney, constructed in accordance with the principles of the present invention.
Figure 3:
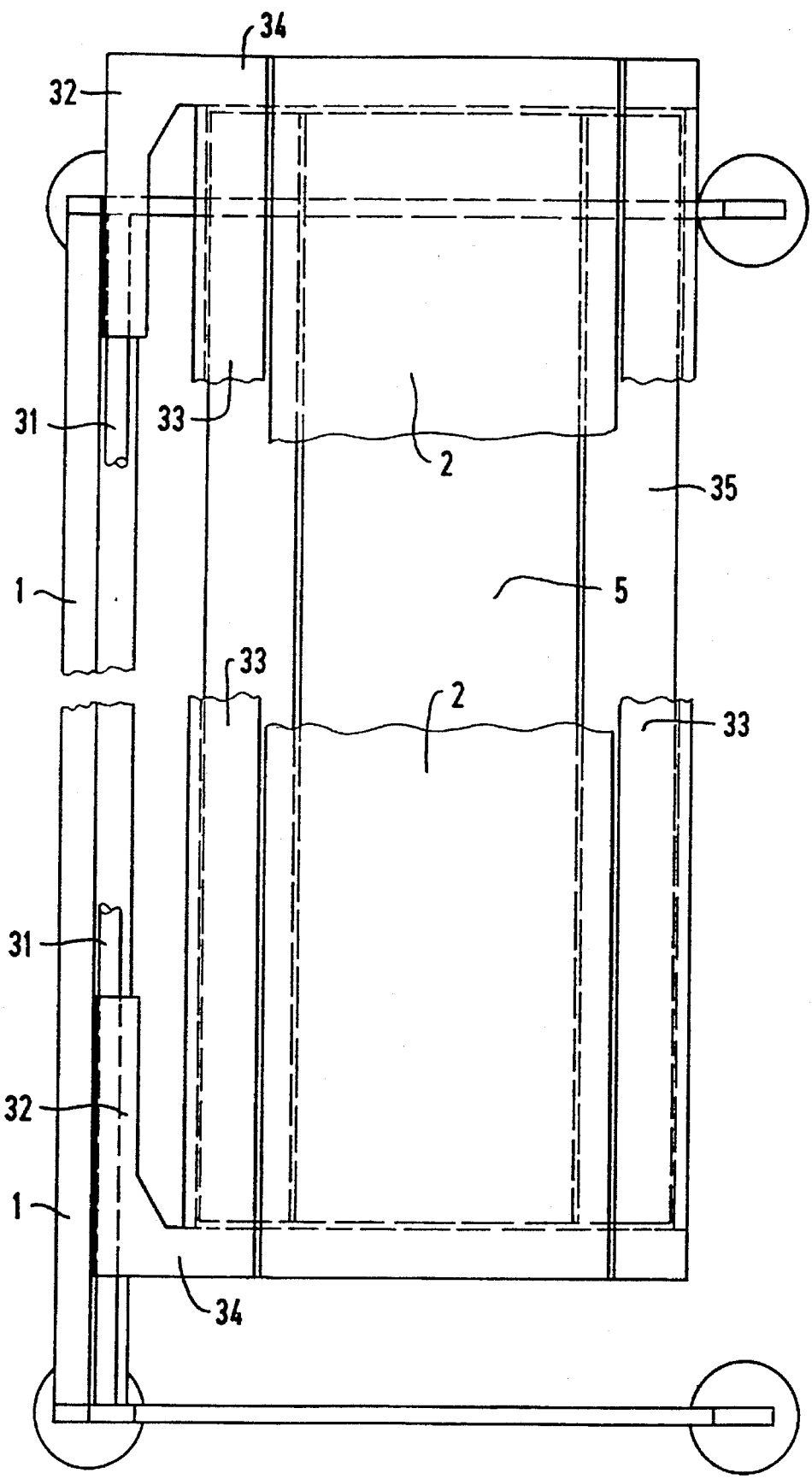
FIG. 3 shows the combination of FIG. 2 in a plan view.

FIGS. 2 and 3 illustrate a preferred embodiment of a patient support operable in combination with a patient gurney for medical examinations, constructed in accordance with the principles of the present invention, wherein element which have already been described above are provided with the same reference numerals.

The combination shown in FIGS. 2 and 3 includes a carriage 1 and a base 4, which is a part of a medical examination apparatus. These components are only schematically shown in FIGS. 2 and 3. In accordance with the principles of the present invention, the carriage 1 has a longitudinal guide 31 extending along the carriage 1, the support plate 2 of the carriage 1 being adjustable by means of the longitudinal guide 31, for example by a frame 32 which slides along the guide 31. In the exemplary embodiment, the frame 32 is formed by two angle elements 33 disposed parallel to the longitudinal guide 31, and spaced from each other, and by two cross beams 34 arranged at the ends of the carriage 1. The cross beams 34 each have a free leg engaging the longitudinal guide 31, the guide 31 being formed by two rails which are offset vertically relative to each other. The longitudinal guide 31 can extend along the entire length of the carriage 1, or may only along a portion of the longitudinal length of the carriage 1. The support plate 2 with the frame 32 can thus be adjusted together along the longitudinal guide 31 over at least a portion of the length of the carriage 1.

If the medical examination apparatus is provided with an adjustably mounted upper part 35, which carries the second support plate 5 in a manner so as to permit displacement in the longitudinal direction relative to the base 4, a transfer of the first support plate 2 onto the second support plate 5 can ensue in a manner as shown in FIG. 2 so that the frame 32 supports itself with its angle elements 33 on the upper part 35, after coupling of the carriage 1 to the base 4, as described above. An interactive mechanical connection thus ensues between the first and second support plates 2 and 5 by means of, for example, pins engaging into recesses. Due to the inventive structure of the carriage 1, the carriage 1 can remain coupled to the base 4 while an examination subject 3, lying on the first support plate 2, is displaced into the opening 6 of the medical apparatus 7. For this purpose, adjustment of the upper part 35 by, for example, 200–500 mm, preferably by 350 mm, ensues first in the direction toward the opening 6, whereby the frame 32 and the first support plate 2 are adjusted together along the longitudinal guide 31. A further adjustment of the two support plates 2 and 5 into the opening 6 follows, possibly together with the examination subject, however, the frame 32 remains at the upper part 35. It is then possible to conduct the examination of the subject.

After completion of the examination, the first support plate 2 can again be accepted by the frame 32, and thus by the carriage 1, in the reverse sequence. In order to prevent an unintentional adjustment of the frame 32 with the first support plate 2 along the guide 31 when transporting the examination subject 3, it is preferable to provide interlock which interlock the frame 32 to the carriage 1 in an initial position of the frame 32. The initial position is the position at which the frame 32 does not project beyond the carriage 1.

Although modifications and changes may be suggested by those skilled in the art, it is the intention of the inventor to embody within the patent warranted hereon all changes and modifications as reasonably and properly come within the scope of his contribution to the art.

I claim as my invention:

1. A system for transferring and supporting a patient comprising:

a patient support apparatus having a stationary base and a longitudinally displaceable first patient support plate; and a patient gurney having a carriage and a second patient support plate, said carriage having a shape for partially surrounding said base when said gurney is disposed adjacent said base and said second support plate, when said gurney is disposed adjacent said base, being held by bearings on said first support plate so as to be co-displaceable therewith, and said carriage having a longitudinal guide permitting longitudinal displacement of said second support plate while said carriage partially surrounds said base without detaching said second support plate from said carriage and without moving said carriage away from said base.

2. An apparatus as claimed in claim 1 wherein said carriage comprises a frame on which said second support plate is mounted, said frame engaging said longitudinal guide by cross beams at opposite ends of said carriage.

3. An apparatus as claimed in claim 1 wherein said carriage has a longitudinal length, and wherein said longitudinal guide is coextensive with said longitudinal length of said carriage.

4. An apparatus as claimed in claim 1 wherein said carriage has a longitudinal length, and wherein said longitudinal guide extends over a portion of said longitudinal length of said carriage.

5. An apparatus as claimed in claim 1 wherein said longitudinal guide comprises rails disposed on said carriage vertically spaced relative to each other.

* * * * *